United States Patent [19]

Assal et al.

[11] Patent Number: 5,373,853
[45] Date of Patent: Dec. 20, 1994

[54] PORTABLE DEVICE FOR THERMAL STIMULUS SENSITIVITY TESTS

[75] Inventors: Jean-Philippe Assal, Conches/Ge, Switzerland; Salvatore Bellinvia, Pordenone; Marino Massarotti, Abano Terme, both of Italy

[73] Assignee: Fidia S.p.A., Abano Terme, Italy

[21] Appl. No.: 62,509

[22] Filed: May 14, 1993

[30] Foreign Application Priority Data

May 15, 1992 [IT] Italy .................... MI92U000481

[51] Int. Cl.$^5$ .................................................. A61B 5/00
[52] U.S. Cl. .......................................................... 128/742
[58] Field of Search ............................ 128/736, 742, 744

[56] References Cited

U.S. PATENT DOCUMENTS

| | | |
|---|---|---|
| 3,274,995 | 9/1966 | Eidus . |
| 4,653,507 | 3/1987 | Laudadio .................. 128/742 |
| 4,763,666 | 8/1988 | Strian et al. ............... 128/742 |
| 5,007,433 | 4/1991 | Hermsdörffer et al. ...... 128/742 |
| 5,060,657 | 10/1991 | Teague ..................... 128/742 |

FOREIGN PATENT DOCUMENTS 0364158 4/1990 European Pat. Off. .

Primary Examiner—Max Hindenburg
Attorney, Agent, or Firm—Hedman, Gibson & Costigan

[57] ABSTRACT

Portable device for thermal stimulus sensitivity tests, in particular for tests in patients affected by neuropathies of diabetic origin, comprising four detecting probes arranged in a single block provided with a handgrip, and each of said probes having a circular metallic outer surface to be placed in contact with the patient's skin and being held by its own adjusting circuit at a pre-set temperature.

3 Claims, 1 Drawing Sheet

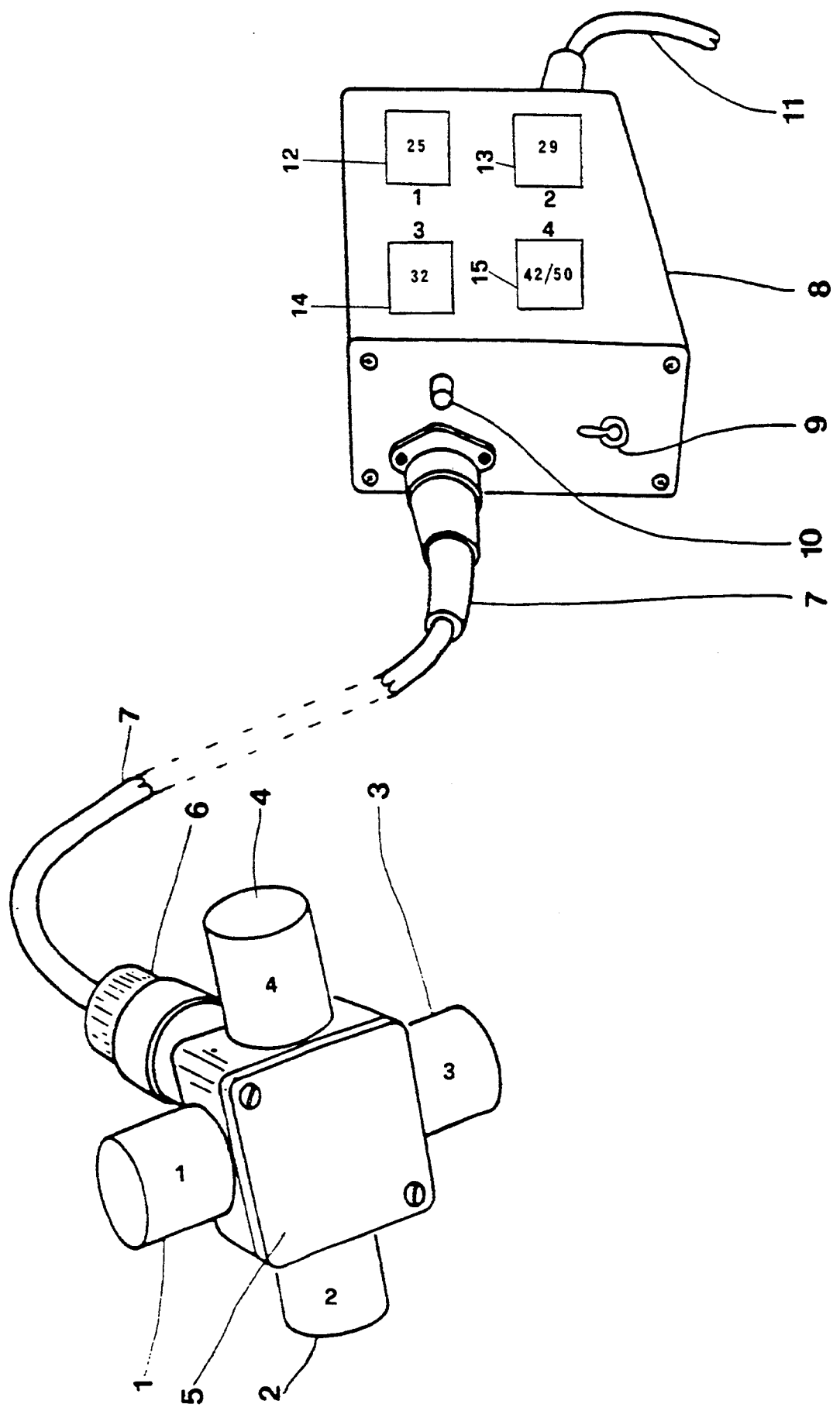

PORTABLE DEVICE FOR THERMAL STIMULUS SENSITIVITY TESTS

FIELD OF THE INVENTION

Portable device for thermal stimulus sensitivity tests, in particular for tests in patients affected by neuropathies of diabetic origin, comprising four detecting probes arranged in a single block provided with a handgrip; each of said probes has a circular metallic outer surface to be placed in contact with the patient's skin and is held by its own control circuit at a pre-set temperature.

The device allows performance of a complete series of significant tests capable of supplying in a very short time (on the order of a few minutes) a reliable evaluation of the patient's sensitivity.

PRIOR ART

Thermal stimulus sensitivity tests are one of the means used in the medical field to verify the peripheral sensitivity of a patient, making evident any neuropathies. To perform such tests a region considered significant, e.g. a malleus, of the cutaneous surface of the patient being examined and on which are rested in rapid succession two bodies, e.g. two probe elements, having different temperatures is stimulated thermally and the patient's ability to discriminate between the two temperatures is appraised. The minimum temperature difference which the patient is able to detect is named 'thermal perception threshold'.

It is observed that in diabetic patients affected by neuropathies even not evident the thermal perception threshold is much higher than that found in patients (including diabetic) who are not neuropathic: in fact in these patients there is observed a progressive reduction of thermal sensitivity which can reach total loss of sensitivity, exposing the neuropathic patient, among other things, to the risk of suffering burns or other lesions, even serious, accidentally and unknowingly.

There are known devices for the performance of thermal stimulus sensitivity tests which comprise a sealed box usually parallelepiped in shape of small dimensions (on the order of a few centimetres) provided with a handgrip for more convenient handling of the device and with at least one probe element (preferable cylindrical) projecting from said box and terminating with a metal cap which is placed in contact with the patient's skin to supply the thermal stimulus used for evaluating the sensitivity. In one possible embodiment of the probe element the surface of the metal cap is on the order of 5 cm².

The outer structure of the sealed box and the side parts of the probe elements on said box are made of electrically and thermally insulating material.

Each probe element contains an independent electrical heating and temperature control circuit of a known type for equipment of this type. To satisfy safety standards in force for this type of equipment the heating and control circuits located in the probe elements are low voltage circuits.

The device for thermal sensitivity tests comprises said sealed box bearing at least one probe element connected by an electric cable to a box containing at least one transformer for supplying with low voltage said electric and/or electronic heating and temperature control circuits of each of the probe elements present on said box, the main switch and one or more warning lights. Said box is connected to the power supply network by a connection cable.

In a first embodiment the known devices comprise a single probe element which can operate at two pre-set temperatures in the range used for the test by acting on the related electric heating and temperature control device. In accordance with another embodiment, also known, the device comprises three probe elements designed to operate at three different fixed temperatures and a fourth probe element which can be made to operate at a temperature selected from a pre-set range.

By way of example the temperature values of the first three probe elements are 25° C., 42° C. and 50° C. respectively while the temperature of the fourth element can be varied in a range of 10° C. (and in particular between 25° C. and 35° C.). The related electric and/or electronic heating and temperature control circuits are controlled by a potentiometer or a "step-by-step" switch or other equivalent means.

Temperature variations in the probe elements induced by contact with the patient's skin are rapidly cancelled by the related heating and control circuits restoring in a very short time the pre-set temperature of the probe element (e.g. for the 50° C. probe there is a maximum restoration time of 10"). This allows performance of the tests at a certain temperature and very short intervals.

BRIEF DESCRIPTION OF THE DRAWING

The drawing is an overview of a thermal stimulus sensitivity test device.

DESCRIPTION OF THE INVENTION

The invention is now described with reference to a nonlimiting embodiment example described in the annexed figure where the sealed box 5 is shown provided with a handgrip 6, the four probe elements 1,2,3,4 and the electric cable 7 which connects it to the box 8 containing at least a transformer for suppluing low voltage to the electric and/or electronic heating and temperature control circuits of each of the four probe elements 1,2,3,4 present on the box 5, the main switch (not shown in the figure), the switch 9 (or other equivalent means) for selecting temperature of the fourth probe element 4, at least one warning light 10 and the cable 11 which connects it to the power supply network.

In the preferred embodiment illustrated in the annexed figure, inside each of the four probe elements 1,2,3,4 is placed a thermometer which measures their temperature instant by instant. The temperatures thus taken are displayed on the corresponding display 12,13,14,15, located on the box 8, which allow the operator to verify before making a test that the probe elements to be used for the test have the required temperatures.

Recent studies performed by comparing the results obtained by applying the thermal stimulus sensitivity test to control groups consisting of neurologically unharmed patients (both diabetic and nondiabetic) divided by age classes and to groups of neuropathic diabetic patients show that the thermal perception threshold increases with age and that for each age class its value is substantially constant and characteristic of the age class.

This means that it is possible to simplify the known instrument described above by assigning to each probe element pre-set temperatures, thus simplifying the electric and/or electronic heating and temperature control circuits located in the sealed box which bears the probe elements. In a preferred embodiment a first probe element 1 is held at the temperature (e.g. 25° C.) taken as reference temperature for the test, two further probe elements 2.3 are held at the temperatures (e.g. 29° C. and 32° C.) respectively corresponding to the thermal perception threshold value of neurologically unharmed patients belonging to two age classes, while the fourth probe element 4 can reach two pre-set temperatures spanning the pain threshold (temperature exceeding which the heat sensation perceived by the patient is replaced by a painful sensation analogous to that produced by a burn). In the preferred embodiment described here the fourth probe element 4 is held at 42° C. or 50° C.

Since with this element there are always available four probe elements constantly at operating condition available at four different temperatures, the tests can be performed in a very short time.

Now there is described briefly a test procedure performed by a device provided in accordance with the present invention. The procedure is interrupted when a test is positive, i.e. when the patient perceives the temperature difference between the two probe elements applied to the same body region (e.g. one of the malleuses). To increase the reliability of the results it is advisable to repeat the test several times for the same pair of temperatures.

The above mentioned studies show that in neurologically unharmed patients (whether diabetic or not) not over 60 years of age the thermal perception threshold is approximately 4° C. while in neurologically unharmed patients (whether diabetic or not) over 60 years of age the thermal perception threshold rises to approximately 7° C.

For a diabetic patient not over 60 years of age the first test is performed with probe elements at 25° C. and 29° C. (hereinafter called '25/29 test'). If the test is positive the patient is neurologically unharmed, otherwise the following test is performed. If the 25/32 test is positive, the patient is a risk patient. He does not evidence neurological lessons but is to be kept under control. If the test is negative the patient can be considered neuropathic. To define the gravity of the neuropathy the following tests are orderly performed:

if the 25/42 test is positive, the patient has a serious neuropathy and requires attentive care;

if the 25/42 test is negative and the 25/50 test is positive, the patient displays a very serious neuropathy and requires especially attentive and assiduous care; if the test is negative the neurological situation of the patient is seriously compromised: in fact, as there is no sensitivity to heat and/or pain (at least locally), the patient is not able to notice if he comes accidentally in contact with flames and/or very hot surfaces and react before suffering even very serious burns.

It is recalled that burns are statistically the biggest cause of accidents in this type of patient.

For a diabetic patient older than 60 the 25/29 test is not significant and is therefore omitted (reducing thus the time required for the examination) and the 25/32 test is performed first.

If this test is positive the patient is neurologically unharmed but otherwise the subsequent tests are performed following the above described procedure.

The above described procedure requires greatly reduced performance times and is therefore particularly advantageous for performance of out-patient's screening to evidence neuropathies in diabetic patients. Indeed, a single test made for the thermal perception threshold significant for the age class to which the patient belongs is sufficient to exclude the presence of any clinically silent neuropathies.

Without going beyond the scope of the present invention it is possible for a skilled person to make in the device object of the present invention all the changes and improvements suggested by normal experience and the natural evolution of the art.

We claim:

1. In a portable device for thermal stimulus sensitivity tests for patients affected by neuropathies of diabetic origin, comprising a sealed box having a shape of a parallelpiped and provided with a handle for holding it and with four cylindrical probe elements electrically connected to said box, each of said probe elements being provided with its own electric and/or electronic heating and temperature control means, the improvement which comprises setting the temperature of three of said probe elements by said control means at different temperatures which are constant and preset while the fourth of said probe elements is held by said electric and/or electronic heating and temperature control means at a temperature selected between two pre-set values spanning the pain threshold.

2. Device in accordance with claim 1, wherein a first probe element of said three probe elements held at a constant temperature is held at the temperature taken as a reference temperature for performing said test, one of said two other probe elements is held at a temperature corresponding to the thermal perception threshold value of neurologically unharmed patients belonging to an age class, the second of said two other probe elements is held at a temperature corresponding to the thermal perception threshold value of neurologically unharmed patients belonging to a second age class, while said fourth probe element can may be set at two pre-set temperatures spanning the pain threshold.

3. Device in accordance with claim 2, wherein said three probe elements are held by said control means at the constant temperature of 25° C., 29° C. and 32° C. respectively while the temperature of said fourth probe element is between 42° C. and 50° C.

* * * * *